United States Patent [19]

Moon

[11] Patent Number: 4,931,732
[45] Date of Patent: Jun. 5, 1990

[54] MAGNETIC FLEXURE SYSTEM FOR DETERMINING SUPERCONDUCTIVE PROPERTIES OF A SAMPLE

[75] Inventor: Francis C. Moon, Ithaca, N.Y.

[73] Assignee: Cornell Research Foundation, Inc., Ithaca, N.Y.

[21] Appl. No.: 223,907

[22] Filed: Jul. 25, 1988

[51] Int. Cl.$^5$ .................... G01N 27/72; G01R 33/12
[52] U.S. Cl. ................................... 324/228; 324/226; 324/262; 505/843
[58] Field of Search ............... 324/205, 207, 209, 226, 324/227, 228, 260, 261, 262; 73/763, 779, 849, 853, 854, 855, 856; 505/843, 856, 851, 825, 842

[56] References Cited

U.S. PATENT DOCUMENTS 2,750,561  6/1956  Gross ................................ 324/228

OTHER PUBLICATIONS

Method for Making Low-Resistivity Contacts to High $T_c$ Superconductors, Ekin et al., Appl. Phys. Lett. 52 (4), 25 Jan. 1988, pp. 331-333.
Equilibrium of a Magnet Floating Above a Superconducting Disk, Williams et al., Appl. Phys. Lett. 52(9), 29 Feb. 1988, pp. 751-752.

Primary Examiner—Reinhard J. Eisenzopf
Assistant Examiner—Walter E. Snow
Attorney, Agent, or Firm—Perman & Green

[57] ABSTRACT

A cantilever beam is employed to place a magnet in proximity to a sample while the sample is maintained at a superconducting temperature. The magnet causes the sample, assuming it is superconductive, to itself generate a magnetic field which interacts with the magnet. Means are provided for measuring the movement of the cantilever beam, such movement being a measure of the interaction of the sample's magnetic field with the magnet. Several types of cantilever beams are disclosed, one of which is adapted to move in a direction orthogonal to the surface of the sample and another of which is adapted to move parallel to the surface of the sample. This enables the obtaining of quantitative measurements of the bulk properties of high temperature superconducting materials.

7 Claims, 4 Drawing Sheets

MAGNETIC FLEXURE SYSTEM FOR DETERMINING SUPERCONDUCTIVE PROPERTIES OF A SAMPLE

FIELD OF THE INVENTION

This invention relates to superconductive materials and, more particularly, to a means for determining the superconductive magnetic properties of a sample. The United States Government has non-exclusive license rights to this invention as a result of partial support by a grant from the National Science Foundation.

BACKGROUND OF THE INVENTION

Since the discovery that certain ceramic materials could be superconducting at temperatures significantly higher than that of liquid helium, the research community has embarked on a wide ranging search for other ceramics having higher critical temperatures (Tc). As of this writing, researchers have found that certain ceramic compositions become superconductive at temperatures in excess of the temperature of liquid nitrogen (77° K.). Almost on a weekly basis, papers are being published disclosing new ceramic materials and compositions which exhibit superconducting properties in the liquid nitrogen regime.

One problem which has received little public notice to date, is that it is difficult to characterize the superconducting properties of these new high Tc materials. On presently used test method involves making electrical contact to a sample and taking measurements of electrical resistance. An obstacle to the application of that method is the high contact resistance that often occurs where the contacts attach to the sample. Efforts have been made to overcome this problem but the preparation of the contacts and the subsequent testing of the superconductor, together, are quite complex. (e.g. see "Method for Making Low-Resistivity Contacts to High Tc Superconductors" by Ekin et al, Applied Physics Letters, Volume 52, Number 4, 25 Jan., 1988).

Others have attempted to determine the qualitative superconducting properties of a material by attempting to float a magnet above the sample. It is known, that when a magnet is bought into proximity with a superconducting sample, its magnetic field induces "super-currents" within the sample. The super-currents then generate their own magnetic field which is repulsive to the field created by the magnet. With the discovery of high Tc superconductors, it has been repeatedly shown that a small magnet can be stably levitated over a superconducting disk. What was surprising from those demonstrations was the finding that a small magnet would float above a superconducting disk at an equilibrium position over the disk's center, stable against lateral displacements. This phenomenon, while interesting, does not provide a quantitative characterization of the material other than simply to say that it is superconducting. There is no indication in such a test as to whether the material exhibits either homogeneous or heterogeneous superconducting properties.

Accordingly, it is an object of this invention to provide a system for determining superconductive properties of a sample which is both simple to operate and sophisticated in its measurement technique.

It is another object of this invention to provide a system for determining superconductive properties of a sample which avoids the necessity for making any connections to the sample.

It is a further object of this invention to provide a system which provides quantitative determinations of the magnetic superconducting properties of a sample.

It is still another object to this invention to provide a system for determining superconductive magnetic properties of a sample which is adapted to determine the homogeneity of the sample's superconducting properties.

SUMMARY OF THE INVENTION

The invention comprises cantilever beam means for suspending magnet means in proximity to a sample while the sample is maintained at a superconducting temperature. The magnet means causes the sample, assuming it is superconductive, to itself generate a magnetic field which interacts with the magnet means in a repulsive manner. Means are provided for measuring the movement of the cantilever beam means when the magnet means is in proximity to the sample, the movement of the cantilever beam means being a measure of the interaction of the sample's magnetic field with the magnetic means. Several types of cantilever beam means are disclosed, one of which is adapted to move in a direction orthogonal to the surface of the sample and another of which is adapted to move parallel to the surface of the sample.

DETAILED DESCRIPTION OF THE INVENTION

Figure 1:
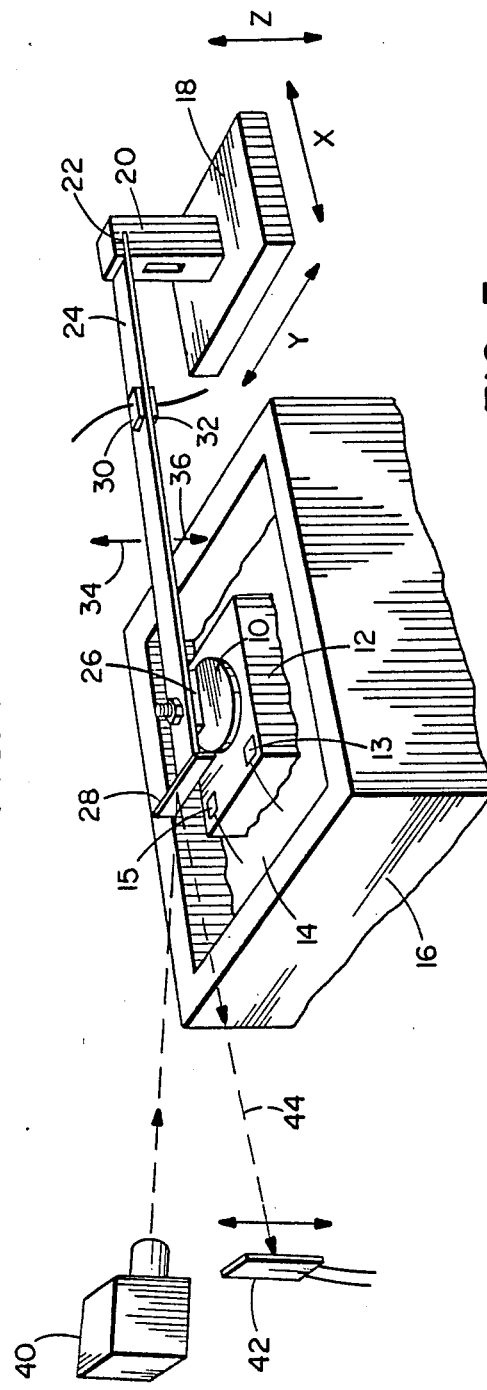
FIG. 1 is an isometric view of a test system which embodies the invention hereof.

Referring now to FIG. 1, a sample of a high temperatures superconducting ceramic (HTSC) material 10 is mounted on an aluminum block 12 which is immersed in a bath of liquid nitrogen 14 contained within insulated tub 16. Also mounted on block 12 is a thermocouple 15. A Hall probe 13 is mounted on the surface of sample 10.

A motorized stage 18 is provided with a vertical support column 20 attached thereto. Motorized stage 18 is provided with motor drives that enable it to move in either of the X, Y or Z directions, as the case may be (not shown). Movable stages of this type are available commercially and may be obtained from the Newport Corporation, P.O. Box 8020, 18235 Mt. Baldy Circle, Fountain Valley, Calif. 92728.

A horizontal slot 22 in column 20 supports the proximal end of a cantilever support beam 24. At the distal end of beam 24, a bar magnet 26 is attached as is a reflecting strip 28. In addition, a pair of strain gauges 30 and 32 are respectively mounted on the upper and lower surfaces of beam 24 to provide an indication of the flexure thereof.

The aspect ratio of beam 24 is such that it exhibits an anisotropic flexibility characteristic, i.e., a substantial flexibility in its thickness dimension and a substantial inflexibility in its width dimension. Thus, beam 24 will flex in a vertical direction as shown by arrows 34 and 36 but not orthogonally thereto. A preferable material for beam 24 is a high strength aluminum alloy, or a non-magnetic stainless steel. Magnet 26 is shown as oriented over sample 10 such that that the axis between its north and south poles is parallel to the surface of sample 10. The system will also provide acceptable measurements if the magnetic axis of magnet 10 is oriented perpendicular to the surface of sample 10. Magnet 26 is preferably a rare earth magnet which exhibits a substantial field strength, (i.e., on the order of at least 2000–3000 Gauss or better at the pole faces). Preferably, magnet 26 is of the samarium cobalt rare earth type with its dipole or polar axis parallel to surface of the sample. Other rare earth magnets are also acceptable (e.g. Nd, Bo, Fe based magnets). It should also be noted that magnet 26 could be replaced by an electromagnetic coil.

A typical position sensing system comprising collimated light source 40 and photo-electric position sensor 42 is provided to indicate the position of magnet 26. Position sensor 42 comprises a plurality of photocells which are successively illuminated as beam 44 moves up and down and which thereby provide outputs indicative of the position of magnet 26 (to thereby provide a position indication for cantilever beam 24). It should be understood, that any position sensor is acceptable so long as it provides a direct positional change indication as magnet 26 is moved.

Figure 3:
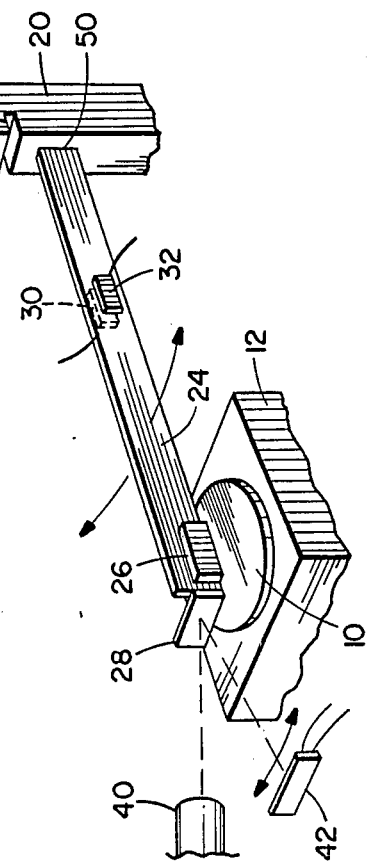
FIG. 3 shows a modification of the test system of FIG. 1 wherein the cantilever beam means is mounted so that it moves parallel to the surface of the sample.
Figure 4:
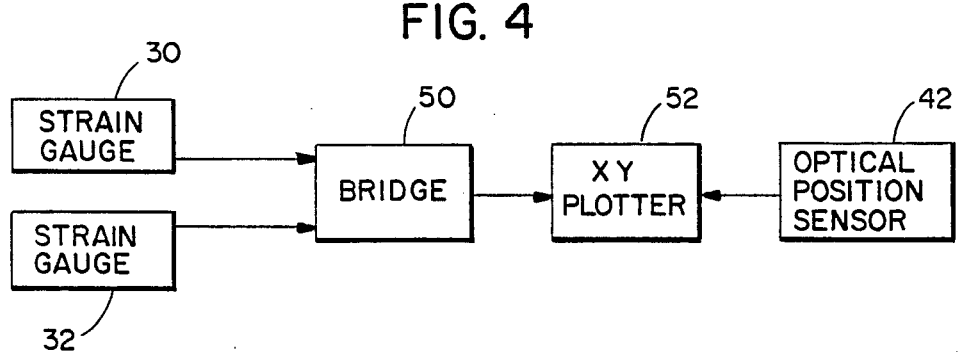
FIG. 4 is a block diagram of analog circuitry which operates in conjunction with systems shown in FIGS. 1, 2 and 3.

Initially, sample 10 is placed on aluminum block 12 and insulated tub 16 (a cryostat) is filled with liquid nitrogen. When sample 10 reaches an equilibrium temperature where it is expected to exhibit superconducting properties, stage 18 moves magnet 26 into proximity with the surface of sample 10. If sample 10 is superconducting, magnet 26 will induce super-currents therein thereby causing sample 10 to produce a magnetic field which opposes the field produced by magnet 26. This interaction causes magnet 26 and beam 24 to deflect in the direction indicated by arrow 34. The deflection of beam 24 results in strain gauges 30 and 32 providing outputs which are a measure of the magnetic force exerted by sample 10. By combining the strain gauge measurements with a measure of the amount of deflection of light beam 24, a plot can be created which shows the variations of magnetic force as the position of magnet 26 is altered. The output from Hall probe 13, which is an indication of the magnetic field strength at the surface of sample 10, can also be plotted against magnetic force. The output from thermocouple 15 provides an indication of temperature and enables a plot of temperature versus force to be produced. The circuitry for providing these measurements and plots is shown in FIGS. 3 and 4 and will be discussed in greater detail hereinbelow.

Figure 2:
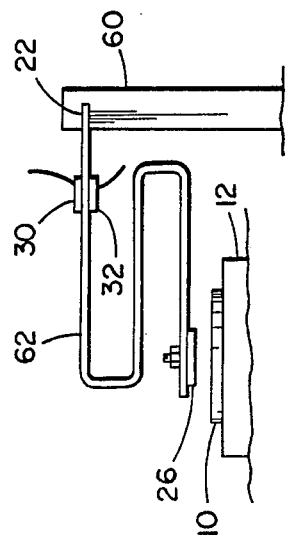
FIG. 2 is a side view of a modification to the test system of FIG. 1 which improves it sensitivity.

A modification of the test system of FIG. 1 which increases its sensitivity is shown in FIG. 2. A taller support column 60 is substituted for column 20 and a folded cantilever beam 62 is substituted for beam 24. Folded beam 62 provides a 3 times more sensitive force indication and a 9 times greater deflection per unit of magnetic force.

The measure of maximum repulsive force provided by strain gauges 30 and 32 provides an indication of the superconducting quality of sample 10. It does not, however, provide an indication of the lateral forces exerted by sample 10. Referring to FIG. 2, beam 24 is removed from slot 22, rotated 90° and inserted into slot 50 so that its main axis of flexibility is now parallel with the surface of sample 10. The position sensing elements of the invention i.e. light source 40, reflector 28 and photoconductor 42 are reoriented so that they are adapted to sense movement in a path parallel to the surface of sample 10.

The interaction between magnet 26 and the fields of force generated by the induced super-currents in sample 10, is then measured by moving column 20 in the Y dimension so that cantilever beam 24 moves magnet 26 across the surface of sample 10. This relative movement allows the interaction between the force fields generated by magnet 26 and sample 10 to be sensed and enables flux pinning to be measured. Flux pinning has the effect of modifying the deflection of beam 24 as it traverses across the surface of sample 10. The variation in deflection of beam 24 is sensed by strain gauges 30 and 32 which, in turn, provide appropriate signals to the measurement circuitry.

This invention can also be used to measure Type I or Type II superconducting behavior. In the Type I regime, the magnetic force is not hysteretic. Thus, by cycling the position of magnet 26, while measuring the magnetic field at the surface of sample 10 with Hall probe 13, one can look for the onset of flux penetration and hysteresis in the outputs from strain gauges 30, 32 as an indication of the transition from Type I to Type II behavior.

Referring now to FIG. 4, an analog system is shown which plots the variations in deflection of beam 24 against the variations in stress in beam 24. The outputs from strain gauges 30 and 32 are fed to a bridge 50 which is adjusted to provide a zero output when cantilever beam 24 and magnet are not under the influence of sample 10's magnetic field (if any). The output from bridge 50 is fed to X, Y plotter 52. When an output from one or the other of strain gauges 30 or 32 predominates, the output from bridge 52 to X, Y plotter 52 is similarly modified. Another input to X, Y plotter 52 comes from photosensor 42. Thus, it can be seen that as the position of magnet 26 is modified with respect to the surface of sample 10, X, Y plotter 52 is provided with signals that enable it to provide a plot of the relationship between the stress in beam 24 and the position of magnet 26.

Figure 5:
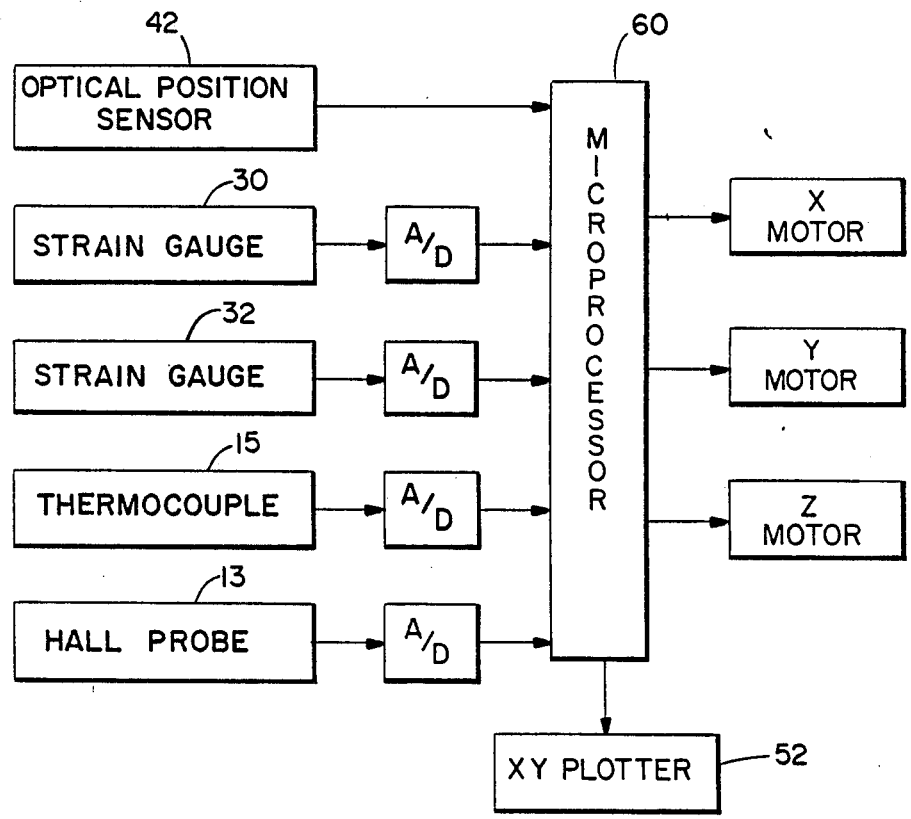
FIG. 5 is a block diagram of a digital system for operation in conjunction with the measurement system shown in FIGS. 1, 2 and 3.

Referring now to FIG. 5, a digital system is shown which enables automatic control of the X, Y and Z motors which control the position of stage 18. In this instance, each of the inputs from photosensor 42 strain gauges 30 and 32, Hall probe 13 and thermocouple 15 are fed to microprocessor 60. In response, microprocessor 60 provides an output to X, Y plotter 52 or any other appropriate display device which is capable of illustrating the relationships indicated by signals from the strain gauges, Hall probe, thermocouple and the position photosensors. In addition, microprocessor 60 can automatically provide signals which operate the X, Y and Z motors to cause the beam 24 to properly move with respect to the face of sample 10 as the measurements are being taken.

EXPERIMENTAL RESULTS

The measurements system described herein, was constructed and used to measure the magnetic forces between a rare earth magnet and a bulk, cylindrically shaped HTSC sample. Cantilever arm 24 was an aluminum alloy and exhibited at least a 8 to 1 aspect ratio in its width to thickness dimensions. The length of the cantilever arm was 32 cm, its width 0.7 cm, and its thickness 0.085 cm. The test magnet was a samarium cobalt rare earth magnet, 6.49 mm long by 6.37 mm in diameter and weighed 1.7 grams. It dipole axis was kept parallel to the surface of the HTSC superconductor.

The superconductor was $Y_1 Ba_2 Cu_3 O_x$ and was processed by the free sintering method. The samples were prepared by a solid state reaction of $Y_2O_3$, $CuO$, and $BaCO_3$. Finely ground powders were calcined for 24 hours in an oxygen atmosphere at 920° C., reground, pressed into pellets, and then free sintered at 950° C. for 12 hours. The density of the sample used was 87% of theoretical density. Its shape was in the form of a cylindrical disc, 18.2 mm in diameter and 5.48 mm thick. The liquid nitrogen was kept level with the HTSC surface.

The test magnet's maximum pole strength was measured at approximately 0.3 Tesla. The field strength normal to the HTSC surface ranged from 0 to 0.075 T.

Figure 6:
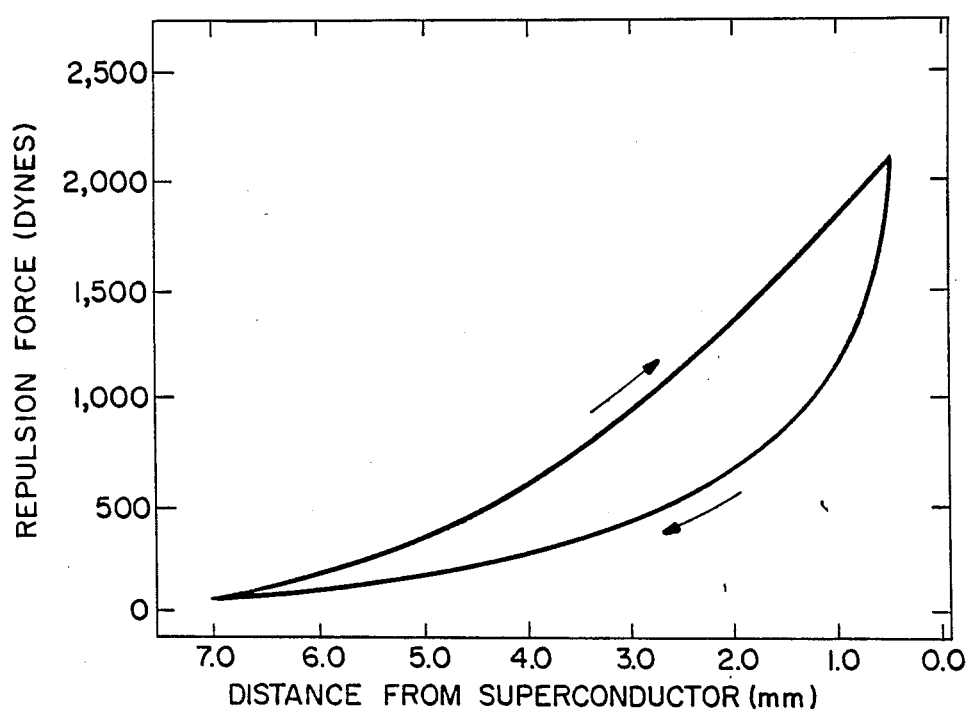
FIG. 6 is a plot for the magnet means of repulsive force versus vertical distance from the superconductor surface.
Figure 7:
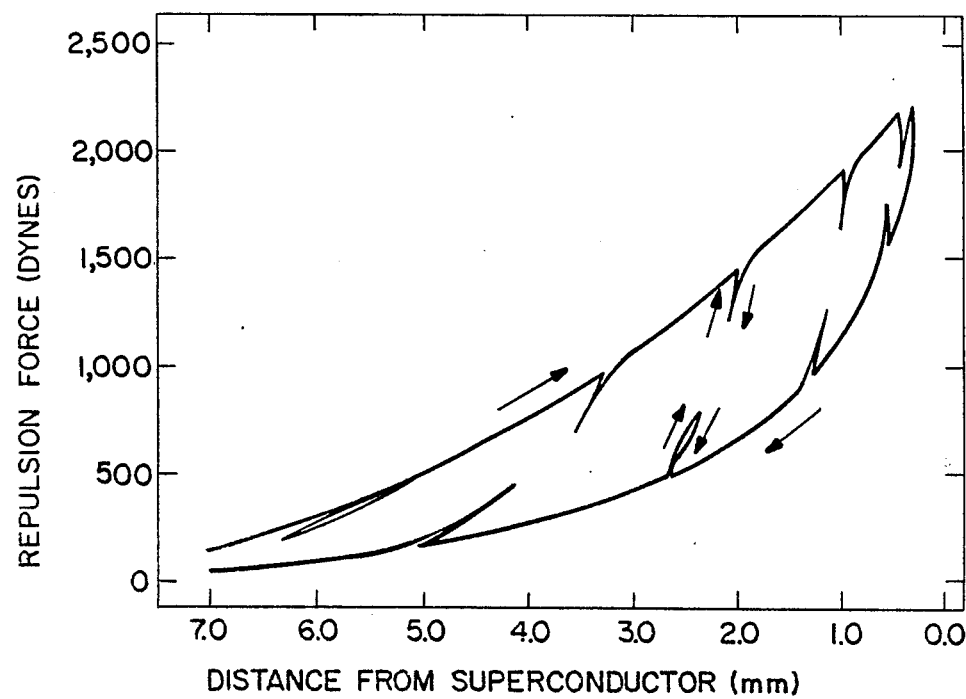
FIG. 7 is a plot similar to FIG. 6 where the movement of the magnet means is modified so that it oscillates at certain positions.
Figure 8:
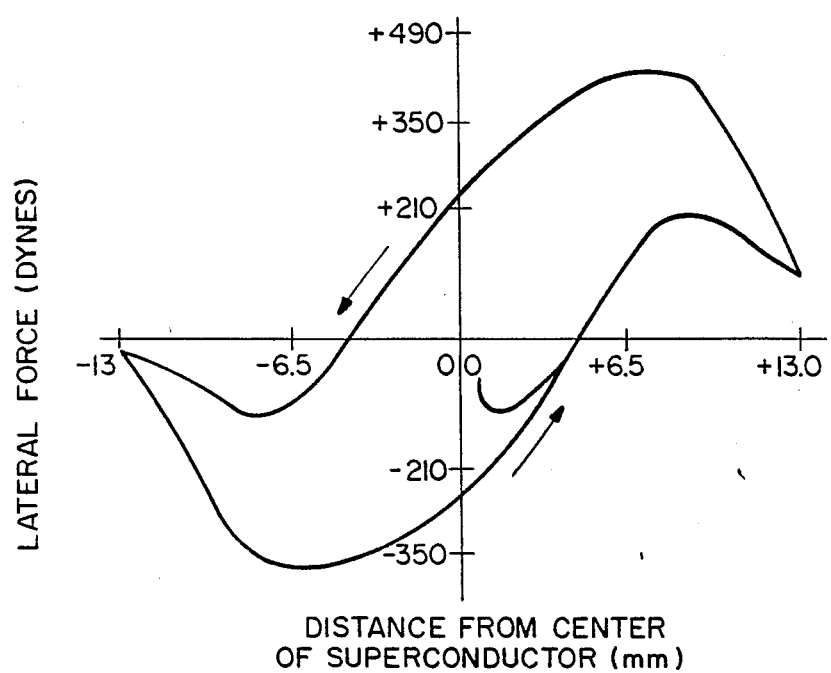
FIG. 8 is a plot similar to FIG. 6 indicating the measurement of lateral forces on the magnet means when it is moved laterally across the surface of the sample.

The results from a series of tests are shown in FIGS. 5-7. Those curves show plots of magnetic force versus distance. The data in FIGS. 5 and 6 are for distances normal to the HTSC surface and those in FIG. 7 are for parallel distances measured from the center of the HTSC disk. The distances shown are measured from the superconductor surface to the bottom surface of the magnet. In each case, the HTSC was first warmed until it went normal and then cooled to the superconducting state before any magnet was brought into proximity.

The repulsion force between the magnet and superconductor was near zero when the magnet was one diameter away as shown in FIG. 5. In this experiment, the magnet was continuously moved toward the superconductor surface and then monotonically moved away using the motorized stage. The data shows a large hysteresis loop. This loop was repeatable when the magnet was recycled through the same movements. The magnetic force equaled the weight of the magnet at both 1.3 mm and 0.5 mm. This suggests that if the magnet were free, there would be two levitated equilibrium positions.

The next experiments involved making small cycles of the distance as shown in FIG. 6. The curves exhibited small hysteresis loops. However, all the small loops were contained in the large hysteresis loop. For very small cycles, the force-distance relationship appeared to approach a reversible behavior which might be a measure of flux pinning. The slope of these small loops is not tangential to the main loop and is also a measure of the magnetic stiffness (flux pinning).

Measurements of the lateral magnetic forces are shown in FIG. 7. In those tests, the superconductor was again brought to its normal state with no magnetic field. The magnet was lowered to a height of 2 mm with its dipole axis parallel to the HTSC surface. Beam 24 was oriented so that it was sensitive to lateral bending and was used to measure the force exerted on the magnet. As shown in FIG. 7, the magnet was moved laterally across the surface from the center to the edge of the superconductor. For the same lateral distance, the lateral force could either act towards or away from the center of the superconductor. Small lateral cycles of motion were also made. As in the cases for the normal force test, the loops created were contained in the major hysteresis loop. The slope of those loops was a measure of the lateral magnetic stiffness (flux pinning).

These results show that a small magnet could be stably levitated on a flat HTSC surface depending on the history of the magnetic flux pattern on the superconductor surface. Once levitated, small magnets will exhibit lateral magnetic stiffness for small excursions. The non-uniqueness of the lateral position of a small levitated magnets above an HTSC disc can be observed. For the force history shown in FIG. 7, there are two lateral equilibrium positions which exhibit zero force. If magnets were initially brought in from the edge of the superconducting disc, then the equilibrium positions would be different as has been indicated by the experiment.

The sensitivity of the measurement system was excellent in that it measured force changes in the 1 to 10 dyne range.

It should be understood that the foregoing description is only illustrative of the invention. Various alternatives and modifications can be devised by those skilled in the art without departing from the invention. Accordingly, the present invention is intended to embrace all such alternatives modifications and variances which fall within scope of the appended claims.

I claim:

1. A system for determining superconductive properties of a sample comprising:
    means for measuring and adjusting the temperature of said sample to a point where said sample is expected to exhibit superconducting properties;
    cantilever beam means for rigidly suspending magnet means at a point of non-contact proximity to said sample to cause said sample to generate a magnetic field if it is superconductive; and
    means for measuring the movement of said cantilever beam means when said magnet means is in said non-contact proximity to said sample, said movement of said cantilever beam means being a measure of the interaction of said generated magnetic field with said magnetic means.

2. The invention as defined in claim 1 wherein said measuring means comprises means for measuring the strain induced in said cantilever beam means.

3. The invention as defined in claim 1 further including means for providing relative movement between said cantilever beam means and said sample to enable said cantilever beam means and magnet means to be brought in and out of proximity with said sample.

4. The invention as defined in claim 1 wherein said cantilever beam means is elastic in a dimension which is orthogonal to a major surface of said sample.

5. The invention as defined in claim 4 wherein said cantilever beam means is folded back upon itself so as to exhibit enhanced properties.

6. The invention as defined in claim 3 wherein said cantilever beam means is a elastic in a dimension which is parallel to a major surface of said sample.

7. The invention as defined in claim 1 further comprising:
    means for measuring the magnetic field at said sample; and
    means for correlating said measurements to provide indications of the relations between the field and temperature.

* * * * *